United States Patent [19]
Kakemoto et al.

[11] Patent Number: 4,900,873
[45] Date of Patent: Feb. 13, 1990

[54] METHOD OF MANUFACTURING PHENOLS FROM LIGNIN

[75] Inventors: Gohki Kakemoto, Tokyo; Hiroshi Sagara; Noriyuki Suzuki, both of Handa; Shogo Kachi, Kashiwa, all of Japan

[73] Assignees: JGC Corporation; Japan Pulp & Paper Research Institute, Inc., both of Tokyo, Japan

[21] Appl. No.: 245,803

[22] Filed: Sep. 19, 1988

[30] Foreign Application Priority Data

Sep. 21, 1987 [JP] Japan ................. 62-234911

[51] Int. Cl.⁴ ............................................. C07C 37/68
[52] U.S. Cl. ................................... 568/761; 568/762; 568/806
[58] Field of Search .................. 568/761, 762, 806

[56] References Cited

U.S. PATENT DOCUMENTS

4,420,644 12/1983 Huiber et al. .................. 568/806

FOREIGN PATENT DOCUMENTS

2104545 3/1983 United Kingdom ............. 568/806

OTHER PUBLICATIONS

Sakakibara et al. "Studies on Hydrolysis of Lignin III", J. Japan Wood Res. Soc., vol. 7, pp. 19–23 (1961) (Japanese/English language).
Sakakibara et al. "Studies on Hydrolysis of Lignin IV", J. Japan Wood Res. Soc., No. 151, pp. 137–153 (1963) (Japanese/English language).
Sakakibara et al. "Studies on Hydrolysis of Lignin V", J. Japan Wood Res. Soc., No. 166, p. 171 (1964) (Japanese/English language).

*Primary Examiner*—Werren B. Lone
*Attorney, Agent, or Firm*—Cushman, Darby and Cushman

[57] ABSTRACT

Phenols such as cresol, phenol and xylenol etc. are obtained by thermal decomposition of a lignin-containing material in a state of a mixture of the lignin-containing material and a double ring aromatic hydrocarbon solvent.

Spent liquid of a solvolysis pulping process can be used as the lignin-containing raw material in the present invention for manufacturing phenols, and the phenols obtained can be utilized as the solvent in the solvolysis process resulting in cost reduction in the pulp production process by self-supplying the necessary solvent in the solvolysis process.

9 Claims, 1 Drawing Sheet

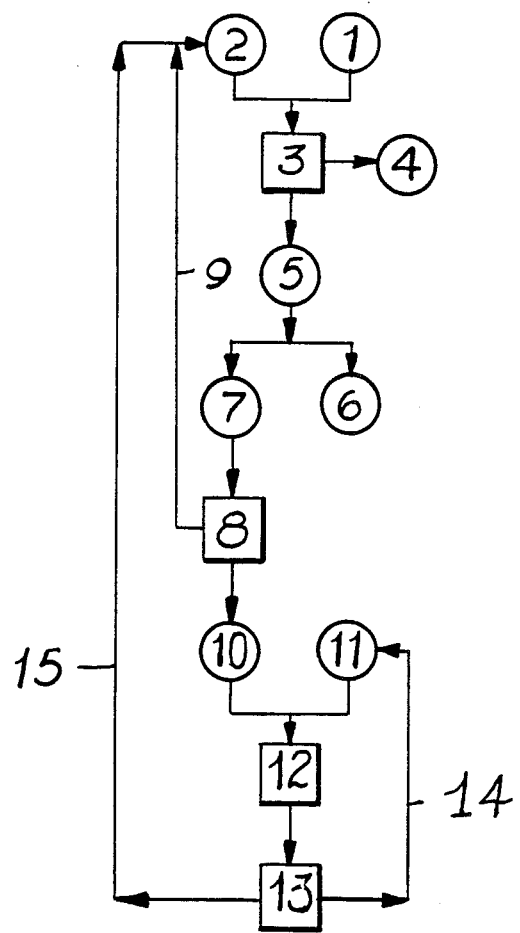

METHOD OF MANUFACTURING PHENOLS FROM LIGNIN

BACKGROUND OF THE INVENTION

1. Field of the Invention

The present invention relates to a method of manufacturing phenols by thermal decomposition of lignin, which is a main ingredient of plant body of wood, bamboo or straw and is obtained as a by-product of paper, pulp production process.

In the chemical pulping process using sulfur-containing-compounds or alkali materials as a lignin-removing agent, lignin obtained as a by-product therefrom is generally burnt up without utilizing it in an effective way.

2. Description of the Prior Art

In Japanese patent public disclosure Tokkaisho 59-163495, a manufacturing process of pulp has been proposed wherein lignin is removed from wood or ligno-cellulosic materials by heating it in a liquid medium consisting of phenols or a mixture of phenols and glycols, and a mixture of water and acetic acid. In this process, it is suggested to make use of phenols obtained by a thermal decomposition or a hydrogenation-decomposition of lignin or a mixture of lignin and hemicellulose formed during the lignin-removing process as aforementioned liquid medium consisting of phenols or a mixture of phenols and glycols. However, no detailed description of conditions for thermal decomposition or hydrogenation-decomposition of lignin or a mixture of lignin and hemicellulose was shown in Tokkaisho 59-163495.

A method is known for manufacturing phenols by hydrogenation-decomposition of lignin, wherein lignin obtained from the residue of wood-saccharizing was treated with hydrogen in the presence of copper-chromite, Co-Mo/diatomaceous earth, Ni-carbonyl or Fe-carbonyl catalyst in a solvent of cyclohexanol at 60-100 kg/cm$^2$G and 380°-400° C. for 0.5-2 hours J. Japan Wood Res. Soc. Vol. 7, page 19-23, (1961); Bulletin of the Government Forest Experiment Station, No. 151, page 137-153, (1963); and Bulletin of the Government Forest Experiment Station, No. 166, pages 159-171, (1964).

However, it has been difficult to obtain phenols effectively by only thermally decomposing lignin (cf. comparative examples described later), and no commercial process of manufacturing phenols by thermal decomposition of lignin has been developed so far.

SUMMARY OF THE INVENTION

It is an object of the present invention to provide a new method of manufacturing phenols by thermal decomposition of lignin, which comprises thermally decomposing a lignin-containing material in a mixture of the lignin-containing material and a double ring aromatic hydrocarbon solvent.

BRIEF DESCRIPTION OF THE DRAWING

The FIGURE is a flow-sheet to explain the present invention applied to a solvolysis process of pulp manufacturing.

DETAILED DESCRIPTION OF THE PREFERRED EMBODIMENTS

The lignin-containing material to be used as a raw material in the present invention can be lignin only or a mixture of lignin and other materials, and can be in a state of a powder-like solid or a liquid.

In detail, lignin separated as an insoluble residue by dissolving carbohydrate of plant body of wood, bamboo, straw or other ligno-cellulosic materials can be used. A lignin solution obtained by treatment of the plant body with an inorganic alkaline chemicals as a delignification reagent, or a lignin solution obtained by treatment of the plant body with an organic reagent such as dioxane, an alcohol etc. as a solvent can also be used. Further, lignin obtained as a residue in wood-saccharization process can be used. Furthermore, lignin-dissolved spent liquid obtained from pulp manufacturing process such as a chemical process or a solvolysis process wherein wood chips are cooked in an organic solvent can be used.

Especially when the spent liquid obtained from the solvolysis process is used as a lignin source in the present invention, phenols such as cresol formed by the present invention is preferably used as a cooking solvent in the solvolysis process. In this case, the raw material of the present invention may be either the spent liquid as it is or after separation of phenols therefrom.

There is no specific limit of lignin concentration in the spent liquid to be used as a lignin source in the present invention. However, because too low a concentration may need too high a quantity of solvent to be used and too high a concentration brings higher viscosity and operational difficulty, the lignin concentration in the spent liquid is desired to be within the range of 4-20 weight percent, preferably 10-15 weight percent for commercial production.

Representative double ring aromatic hydrocarbon solvent includes naphthalene, alkylnaphthalene having at least one alkyl group of 1-3 carbon atoms, biphenyl etc. One selected therefrom or a mixture thereof can be used.

The optimum thermal decomposition reaction conditions depend upon the kind of double ring aromatic hydrocarbon solvent used. Generally speaking, the practical range of the reaction temperature is within the range of 260°-400° C., preferably 280°-400° C., the reaction pressure is within the range of 5-100 kg/cm$^2$G, preferably 5-60 kg/cm$^2$G, more preferably 10-60 kg/cm$^2$G and the reaction time is within the range of 5-180 minutes, preferably 10-120 minutes.

When a lower temperature is adopted, the solvent does not give enough effect on the reaction to decrease its dissolving ability. On the contrary, when a higher temperature is adopted, the recovery rate of phenols goes down, as the formation of gas and solid (carbide) would be increased due to the decomposition or polymerization and condensation of lignin.

It is preferable to lengthen the time when a lower temperature is adopted and to shorten the time when a higher temperature is adopted.

A preferable range of the solvent concentration in the mixture of a lignin-containing material and a solvent is 20-70 weight percent, more preferably it is 40-60 weight percent.

In the present invention, the double ring aromatic hydrocarbon solvent is supposed to work as an extractant of phenols in the reaction. Namely, in the presence of the double ring aromatic hydrocarbon solvent, phenols such as cresol, xylenol or phenol formed by thermal decomposition of lignin are seized effectively by the solvent without binding with lignin again, then recovered.

The general requirements for the extractant in the manufacturing of phenols by thermal decomposition of lignin are: (1) to dissolve phenols in it easily, (2) to have lower reactivity with lignin, (3) to have low thermal decomposition property, (4) to have different boiling point or melting point from those of phenols, (5) to have high critical temperature (to enable thermal decomposition reaction in liquid state and keep high solubility of phenols in it), (6) to have lower melting point. (for easy handling), (7) to have low vapor pressure. (to keep away from high pressure state of thermal decomposition reaction).

The double ring aromatic hydrocarbon solvent such as 1-methyl naphthalene, biphenyl or naphthalene etc. satisfies the aforementioned requirements.

FIG. 1 is a flow-sheet to explain the present invention applied to a solvolysis pulp manufacturing process.

A mixed solvent(2) of cresol and water is added to wood chips(1) and cooked in a cooking vessel(3) at 185° C. for 210 minutes for example, and pulp(4) and solvolysis spent liquid(5) which contains about 4 wt.% of lignin are obtained. The solvolysis spent liquid(5) is separated to inorganic phase(6) and organic phase(7). The organic phase(7) is distilled in a vacuum distillation tower(8) to give cresol and concentrated spent liquid(10) dissolving about 12-15 wt.% of lignin. (Degree of the concentration is preferably one-third, from the view point of the viscosity of the liquid). Cresol is recovered by line(9) and is used in the cooking vessel(3) again.

The lignin-dissolving concentrated spent liquid(10) is mixed with a double ring aromatic hydrocarbon solvent(11) in a predetermined ratio, and thermally decomposed in a reactor(12) at a pre-determined conditions and phenols are produced from lignin. Materials obtained by the thermal decomposition of lignin are separated by distillation at a distillation tower(13) to phenols and the double ring aromatic hydrocarbon solvent. The double ring aromatic hydrocarbon solvent is recovered by a line(14) to recycle and phenols are recovered by a line(15) to be used in the cooking process.

In the solvolysis pulp manufacturing process using phenols as a cooking solvent (delignification reagent), the cooking of wood chips is performed under conditions of a temperature of 100°-250° C., a weight ratio of the cooking solvent (a mixture of phenols and water) to wood chips of 3-10 times, and the treatment time of 1-5 hours.

In this manner, spent liquid of a solvolysis pulping process can be used as the lignin-dissolving raw material in the present invention for manufacturing phenols, and the phenols obtained can be utilized as the solvent in the solvolysis process resulting in cost reduction in the pulp production process by self-supplying the necessary solvent in the solvolysis process.

For a better understanding of the present invention, the following comparative examples of thermal decomposition reaction without using solvents and examples of thermal decomposition in the presence of double ring aromatic hydrocarbon solvents are provided.

COMPARATIVE EXAMPLES 1-4

50 grams of concentrated spent liquid of solvolysis pulping process (containing ingredient composed of 13.3 wt% of lignin, 59.2 wt% of cresol, 0.3 wt% of xylenol, a negligible amount of phenol and 27.2 wt% of high boiling points materials) were introduced into a 200 cc autoclave. After replacement of the air in the autoclave with nitrogen, the fluid was thermally decomposed with agitation at 300° C. for 30 minutes (Comparative Example 1), at 350° C. for 10 minutes (Comparative Example 2), at 400° C. for 10 minutes (Comparative Example 3) and at 450° C. for 10 minutes (Comparative Example 4).

Thermally decomposed products were analyzed by gaschromatography after dissolving it in dioxane.

Increasing rate of phenols (sum of phenol, cresol and xylenol) is calculated by the following equation (1) and increasing rate of cresol is calculated by the following equation (2).

$$\text{increasing rate of phenols} = \frac{\text{phenols in decomposed products} - \text{phenols in raw materials}}{\text{phenols in raw materials}} \times 100 \quad (1)$$

$$\text{increasing rate of cresol} = \frac{\text{cresol in decomposed products} - \text{cresol in raw materials}}{\text{cresol in raw materials}} \times 100 \quad (2)$$

Test results are shown in Table 1.

TABLE 1

| Comparative Example No. | decomposition condition | | | increasing rate | |
|---|---|---|---|---|---|
| | temp. °C. | pressure*[1] kg/cm²G | Time min. | phenols wt. % | (cresol) wt. % |
| 1 | 300 | 30 | 30 | 0 | (0) |
| 2 | 350 | 55 | 10 | −2.7 | (−3.8) |
| 3 | 400 | 75 | 10 | −13.8 | (−23.2) |
| 4 | 450 | 100 | 10 | −19.0 | (−33.3) |

*[1] measured at the end of the thermal decomposition

It is understood that at higher temperature than 350° C., phenols existed in the concentrated spent liquid of solvolysis pulping process are decomposed and phenols cannot be recovered from lignin. At lower temperature than 300° C., neither increase nor decrease of phenols was observed.

EXAMPLE 1

(solvent: 1-methylnaphthalene)

50 grams of concentrated spent liquid of solvolysis pulping process as used in Comparative Examples and 50 grams of 1-methylnaphthalene were introduced into a 200 cc autoclave. After replacement of the air in the autoclave with nitrogen, the temperature was raised to that as shown in Table 2, and the spent liquid was thermally decomposed with agitation for the period as shown in Table 2.

Thermally decomposed products were analyzed by gaschromatography after dissolving it in dioxane.

Test results are shown in Table 2.

TABLE 2

| Example No. | decomposition condition | | | increasing rate | |
|---|---|---|---|---|---|
| | temp. °C. | pressure*[1] kg/cm²G | Time min. | phenols wt. % | (cresol) wt. % |
| 1-1 | 280 | 8 | 60 | 12.5 | (2.6) |
| 1-2 | 300 | 9 | 30 | 2.5 | (0) |
| 1-3 | 300 | 10 | 60 | 11.1 | (2.4) |
| 1-4 | 310 | 12 | 60 | 6.1 | (1.2) |
| 1-5 | 350 | 15 | 20 | 2.2 | (0.4) |

*[1] measured at the end of the thermal decomposition

Within the range of 280°-350° C. and 20-60 minutes, phenols are formed. It is understood that at the same decomposition time (60 minutes), the lower the temperature is, the higher the increasing rate of phenols becomes, and at the same decomposition temperature (300° C.), the longer the reaction time is, the higher the increasing rate of phenols becomes.

EXAMPLE 2

(solvent: biphenyl)

50 grams of concentrated solvolysis spent liquid same as used in Comparative Examples and 50 grams of biphenyl were introduced into 200 cc autoclave. After replacement of the air in the autoclave with nitrogen, the temperature was raised to that as shown in Table 3 and the spent liquid was thermally decomposed with agitation for the period as shown in Table 3.

Thermally decomposed products were analyzed by gaschromatography after dissolving it in dioxane.

Test results are shown in Table 3.

TABLE 3

| Example No. | decomposition condition | | | increasing rate | |
|---|---|---|---|---|---|
| | temp. °C. | pressure*1 kg/cm²G | Time min. | phenols wt. % | (cresol) wt. % |
| 2-1 | 300 | 8 | 30 | 0.9 | (−0.2) |
| 2-2 | 300 | 8 | 60 | 2.0 | (0.7) |
| 2-3 | 340 | 15 | 60 | 14.8 | (9.4) |
| 2-4 | 350 | 18 | 30 | 8.5 | (3.5) |
| 2-5 | 350 | 19 | 60 | 18.3 | (10.7) |
| 2-6 | 350 | 22 | 120 | 13.5 | (9.5) |
| 2-7 | 397 | 37 | 10 | 1.5 | (−9.6) |

*1measured at the end of the thermal decomposition

Within the range of 300°–397° C. and 10–120 minutes, especially 340°–350° C., increasing rate of phenols goes up and the longer the reaction time becomes, the increasing rate of phenols goes up, but too long a reaction time gives a slower increase. For example, at 397° C., shorter reaction time will be required.

EXAMPLE 3

(solvent: naphthalene)

50 grams of concentrated solvolysis spent liquid same as used in Comparative Examples and 50 grams of naphthalene were introduced into 200 cc autoclave. After replacement of the air in the autoclave with nitrogen, the temperature was raised to that as shown in Table 4 and the spent liquid was thermally decomposed with agitation for the period shown in Table 4.

Thermally decomposed products were analyzed by gaschromatography after dissolving it in dioxane.

Test results are shown in Table 4.

TABLE 4

| Example No. | decomposition condition | | | increasing rate | |
|---|---|---|---|---|---|
| | temp. °C. | pressure*1 kg/cm²G | Time min. | phenols wt. % | (cresol) wt. % |
| 3-1 | 300 | 6 | 30 | 0.9 | (−0.2) |
| 3-2 | 300 | 6 | 60 | 1.0 | (−1.9) |
| 3-3 | 348 | 16 | 60 | 4.0 | (−1.6) |
| 3-4 | 350 | 16 | 30 | 0.6 | (−1.3) |
| 3-5 | 400 | 33 | 10 | 11.8 | (2.6) |

*1measured at the end of the thermal decomposition

At 400° C., comparatively shorter reaction time will be enough for the purpose, but at lower temperature side, comparatively longer reaction time will be required.

I claim:

1. A method of manufacturing phenols from lignin which comprises the following steps:
   dissolving plant lignin-cellulosic material in an organic or inorganic lignin removing solvent resulting in a lignin-containing material, said lignin-containing material being a lignin solution or by separating said lignin from said solution, a solid lignin-containing residue;
   mixing said lignin-containing material with a double ring aromatic hydrocarbon solvent; and
   decomposing said mixture at a temperature of 260°–400° C., under a pressure of 5–100 kg/cm²G, for a time period of 5–180 minutes.

2. A method of manufacturing phenols from lignin according to claim 1, wherein said double ring aromatic hydrocarbon solvent is the one or more selected from the group consisting of naphthalene, alkylnaphthalenes and biphenyl.

3. A method of manufacturing phenols from lignin according to claim 1, wherein the concentration of the double ring aromatic hydrocarbon solvent in the mixture of the lignin-containing material and the solvent is within the range of 20–70 weight percent.

4. A method of manufacturing phenols from lignin according to claim 1, wherein the lignin-containing material in the form of a lignin solution is a spent liquid obtained from a pulp manufacturing process.

5. A method of manufacturing phenols from lignin according to claim 4, wherein the pulp manufacturing process is a solvolysis pulp manufacturing process wherein wood chips are cooked in an organic solvent.

6. A method of manufacturing phenols from lignin according to claim 5, wherein the organic solvent in the solvolysis pulp manufacturing process contains phenols, and a lignin-dissolving spent liquid obtained from the solvolysis pulp manufacturing process is thermally decomposed in a state of a mixture of the lignin-dissolving spent liquid and a double ring aromatic hydrocarbon solvent, and phenols formed by the thermal decomposition of lignin is separated from the double ring aromatic hydrocarbon solvent to be recycled to the solvolysis pulp manufacturing process.

7. A method of manufacturing phenols from lignin according to claim 4, wherein the concentration of lignin in the lignin-dissolving spent liquid is 4–20 weight percent.

8. A method of manufacturing phenols from lignin according to claim 7, wherein the concentration of lignin in the lignin-dissolving spent liquid is 10–15 weight percent.

9. A method of manufacturing phenols from lignin according to claim 1, wherein the temperature is in the range of 280°–400° C., the pressure is in the range of 5–60 Kg/cm²G and the time period is in the range of 5–180 minutes.

* * * * *